United States Patent [19]

Mignani et al.

[11] Patent Number: 4,543,433
[45] Date of Patent: Sep. 24, 1985

[54] TETRAENE, ITS PREPARATION AND ITS USE

[75] Inventors: Gerard Mignani, Lyons; Didier Morel, Villiers Sur Orge, both of France

[73] Assignee: Rhone-Poulenc Sante, Courbevoie, France

[21] Appl. No.: 694,077

[22] Filed: Jan. 23, 1985

[30] Foreign Application Priority Data

Jan. 26, 1984 [FR] France ............... 84 01198

[51] Int. Cl.⁴ .................. C07C 1/30; C07C 11/21
[52] U.S. Cl. .................. 585/16; 585/638; 585/641
[58] Field of Search ........... 585/16, 638, 641, 642

[56] References Cited

U.S. PATENT DOCUMENTS

| 3,325,555 | 6/1967 | Geburn | 585/16 |
| 3,691,250 | 9/1972 | Coulson | 585/16 |
| 3,859,374 | 1/1975 | Komatsu et al. | 585/16 |
| 3,925,497 | 12/1975 | Josey et al. | 585/16 |
| 3,970,592 | 7/1976 | Ploner | 585/16 |

Primary Examiner—D. E. Gantz
Assistant Examiner—A. Pal
Attorney, Agent, or Firm—Stevens, Davis, Miller & Mosher

[57] ABSTRACT

The new tetraene of formula:

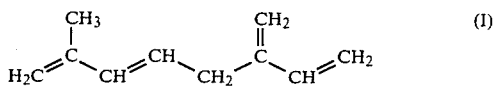

is useful particularly as an intermediate in the synthesis of, for example, hexahydropseudoionone, pseudoionone and vitamin A.

It may be made by dehydrochlorinating 3-chloro-2-methyl-6-methylene-1,3,7-octadiene in the presence of a palladium catalyst and an inorganic base.

7 Claims, No Drawings

TETRAENE, ITS PREPARATION AND ITS USE

The present invention provides the new tetraene, 2-methyl-6-methylene-1,3,7-octatriene, which has the formula:

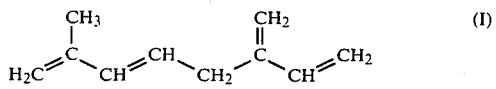

and a process for its preparation from 3-chloro-2-methyl-6-methylene-1,7-octadiene.

It is known, particularly from the work of J. Tsuji, Tetrahedron Letters, 24, 2075–2078 (1978) and Ann. New-York Acad. Sciences., 260 (1980) or that of Chaci. J. of Molecular Catalysis, 19, 189–200 (1983), to carry out elimination reactions employing, as catalyst, derivatives of palladium(II) or of palladium(O) in the presence of a ligand. However, these reactions are not always selective and frequently result in the formation of isomeric products which are difficult to separate.

According to the present invention, 2-methyl-6-methylene-1,3,7-octatriene of formula (I) is obtained by dehydrochlorinating 3-chloro-2-methyl-6-methylene-1,7-octadiene (or 3-chloromyrcene) in the presence of a catalyst based on divalent palladium or on palladium (O) combined with a ligand and of an inorganic base, and optionally a quaternary ammonium salt. Under these conditions, 2,6-dimethyl-1,3,5,7-octatetraene (or cosmene) is not formed.

Particularly suitable divalent palladium derivatives which may be mentioned are PdCl$_2$, Pd(OCOCH$_3$)$_2$, Pd(NO$_3$)$_2$, Pd(acetylacetonato)$_2$, PdCl$_2$(PPh$_3$)$_2$, PdCl$_2$(PhCN)$_2$, PdCl$_2$(CH$_3$CN)$_2$, (C$_3$H$_5$PdCl)$_2$, (C$_3$H$_5$PdOCOCH$_3$)$_2$, and (C$_3$H$_5$)$_2$Pd.

Zero-valent palladium derivatives which are particularly suitable are Pd(dibenzylidene acetone)$_2$ and derivatives of the type PdL$_4$ in which L denotes a ligand chosen from phosphines, diphosphines, phosphites, arsines and stibines. Derivatives of phosphorus, arsenic and antimony, such as phosphines, arsines and stibines, are particularly suitable as ligands combined with the palladium derivatives.

In general, a molar quantity of catalyst of between 0.01 and 0.1 per mole of 3-chloromyrcene is employed.

The inorganic base required for the process of the invention is generally an alkali metal hydroxide, such as sodium hydroxide or potassium hydroxide, in the form of a finely ground powder. In general, an equimolar quantity of base is employed relative to the 3-chloromyrcene employed.

In order to promote the rate of reaction, it is particularly advantageous to add a quaternary ammonium salt such as tetrabutylammonium chloride, bromide or sulphate to the reaction mixture. It is also possible to employ tetrabutylammonium hydroxide. In general, 0.05 to 0.2 mole of quaternary ammonium salt is used per mole of 3-chloromyrcene.

The reaction is preferably carried out in an anhydrous organic solvent which is an ether such as diethyl ether or tetrahydrofuran or an aromatic hydrocarbon such as benzene or toluene.

To avoid polymerization of the product, the reaction is, preferably, carried out at a temperature below 25° C.

The product of formula (I) is isolated from the reaction mixture in accordance with the usual techniques after the catalyst has been removed.

2-Methyl-6-methylene-1,3,7-octatriene of formula (I) is particularly useful as an intermediate for compounds useful in the synthesis of vitamin A.

Thus, when subjected to the action of a compound containing an active methylene group, such as methyl acetylacetate, under the conditions described in European Specification No. 44,771A, corresponding to U.S. Pat. No. 4,460,786 in the name of Didier Morel, the contents of which are incorporated herein by specific reference, the product of formula (I) gives the product of formula:

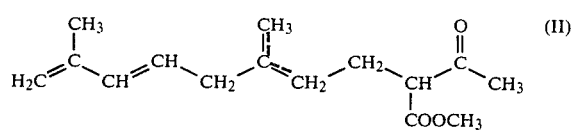

which, after decarboxylation and hydrogenation, yields tetrahydrogeranylacetone or hexahydropseudoionone.

The product of formula (II), after decarboxylation, may be isomerized to pseudoionone by being heated in the presence of a rhodium-based catalyst.

The following Examples illustrate the invention.

EXAMPLE 1

Into a 250-cc round flask are introduced, under an argon atmosphere: finely ground sodium hydroxide (11.98 g; 299.5 millimoles), triphenylphosphine (3.59 g; 15.1 millimoles), tetrabutylammonium chloride (2.76 g; 9.9 millimoles) and [(C$_3$H$_5$)$_2$PdCl]$_2$ (1.09 g; 3 millimoles). After the apparatus has been purged three times with argon, anhydrous tetrahydrofuran (100 cc) and 3-chloromyrcene (53.26 g; 312 millimoles) are added. The mixture is kept at a temperature of about 20° C. for 20 hours. Water (100 cc) is then added, and the reaction mixture is extracted with pentane (3×50 cc). The combined organic layers are dried over magnesium sulphate. After filtration and evaporation of the solvent, a yellow oil (51.94 g) is obtained. By distillation under reduced pressure, a colourless oil (27.2 g) is obtained, containing 93.3% of 2-methyl-6-methylene-1,3,7-octatriene (b.p.=54° C. at 9 mm Hg; 1.2 kPa).

Analysis by gas phase chromatography using an internal standard makes it possible to establish that:

the degree of conversion of 3-chloromyrcene is 94.6% the yield of 2-methyl-6-methylene-1,3,7-octatriene is 86.3% based on the 3-chloromyrcene converted.

The structure of 2-methyl-6-methylene-1,3,7-octatriene is confirmed by the infrared spectrum, the proton nuclear magnetic resonance spectrum, the ultraviolet spectrum and the mass spectrum.

The 3-chloromyrcene employed as starting product may be prepared as follows:

A 4-liter reactor is employed, fitted with a mechanical stirrer, a thermometer, a gas bubbler device, a pentane inlet (controlled by a pump), and a distillation column, the outlet of which is connected to a 5-liter round flask containing 1.5N sodium hydroxide solution which is circulated by a pump downwards through a column packed with Raschig rings mounted above the round flask (in order to remove the hydrochloric acid entrained by the pentane) and itself connected to a round flask in which the pentane is condensed.

In the reactor are placed, under an argon atmosphere, pure myrcene (840 g; 6.176 moles) and pentane (2 liters). The flask is heated in a bath at 45°–55° C. The temperature of the reaction mixture is 35° C. A gaseous mixture of chlorine and argon is then passed into the reactor, the ratio of chlorine to argon being 7/12. Pentane and the hydrochloric acid formed are removed by distillation while pentane is simultaneously added to maintain a constant volume. The rate of addition of chlorine is 167 g/hour and that of pentane 2 liters/hour. After 2 hours and 40 minutes, 440 g of chlorine (6.19 moles) and 5 liters of pentane have been added. The volume of pentane collected is 5.5 liters. After chlorine addition has ended, the pentane present in the reactor is removed by distillation at 40° C. under 5.3 kPa. A residue (1.080 g) is thus obtained, which is distilled quickly at between 34° and 60° C. at 0.08 kPa. The distillate obtained (1,026 g) assays at 86.9% 3-chloromyrcene. The yield is 84.6% based on the myrcene employed.

Determination of myrcene in the light distillates shows that the degree of conversion is 96.4%. The yield is 87.8% based on the myrcene which has reacted.

EXAMPLE 2

Into a 250-cc round flask are introduced, under an argon atmosphere: finely ground sodium hydroxide (13.0 g; 325 millimoles), Pd[P($C_6H_5$)$_3$]$_4$ (1 g; 0.74 millimole), and tetrabutylammonium chloride (2.86 g; 10.3 millimoles). After purging 3 times with argon, anhydrous tetrahydrofuran (100 cc) and 3-chloromyrcene (47 g; 275.4 millimoles) are added. The mixture is stirred at a temperature of about 20° C. for 48 hours. Water (100 cc) is added and the mixture is then extracted with pentane (3×20 cc). The combined organic phases are dried over magnesium sulphate. After filtration and evaporation of the solvent, a yellow oil (26.31 g) is obtained. After distillation under reduced pressure, a colourless oil (14.21 g) is obtained, containing 89.6% of 2-methyl-6-methylene-1,3,7-octatriene, by vapour phase chromatographic analysis.

Gas phase chromatographic analysis using an internal standard makes it possible to establish that:

the degree of conversion of 3-chloromyrcene is 94.5% the yield of 2-methyl-6-methylene-1,3,7-octatriene is 53.2% based on the 3-chloromyrcene converted.

EXAMPLE 3

Into a 500-cc round flask are introduced, under an argon atmosphere: sodium carbonate (5.32 g; 50.2 millimoles), tri(m-sulphophenyl)phosphine (10.65 g; 17.04 millimoles, as its sodium salt (Na TPPTS)), and [RhCl(1,5-cyclooctadiene)]$_2$ (0.38 g; corresponding to 1.54 millimole of rhodium). After purging 3 times with argon, a water-methanol mixture (75-25 by volume; 100 cc) is added, followed by methyl acetylacetate (80 cc; 742 millimoles) and 2-methyl-6-methylene-1,3,7-octatriene (33.6 g; 248.5 millimoles), the purity of which is 92.5% (according to gas phase chromatographic analysis). The mixture is stirred at 60° C. for 24 hours. After separation, the aqueous phase is extracted with ether (100 cc). The combined organic phases are washed with water (50 cc) and then dried over magnesium sulphate. After filtration and evaporation of the solvent, a dark red oil (60.88 g) is obtained.

Analysis by gas phase chromatography shows that the degree of conversion of 2-methyl-6-methylene-1,3,7-octatriene is 98%.

Spectral analyses (NMR, infrared, mass) show that the product obtained consists of a 55/45 mixture of products of formula:

CH$_2$=C(CH$_3$)—CH=CH—CH$_2$—C(CH$_3$)=CH—CH$_2$—CH(COOCH$_3$)—CO—CH$_3$ and
CH$_2$=C(CH$_3$)—CH=CH—CH$_2$—C(=CH$_2$)—CH$_2$—CH$_2$—CH(COOCH$_3$)—CO—CH$_3$ A 4N sodium hydroxide solution (60 cc) is added to the product thus obtained (60.88 g) dissolved in methanol (60 cc). The solution is stirred vigorously for 3 hours at a temperature of 45° C.

The reaction mixture is neutralized by adding 50% sulphuric acid. After extraction with ether (100 cc), a light yellow oil (57.95 g) is obtained. After distillation at 118°–120° C. under reduced pressure (3 mm Hg; 0.4 kPa), a mixture (15.99 g) of the isomeric products of formula:

CH$_2$=C(CH$_3$)—CH=CH—CH$_2$—C(CH$_3$)=CH—CH$_2$—CH$_2$—CO—CH$_3$
CH$_2$=C(CH$_3$)—CH=CH—CH$_2$—C(=CH$_2$)—CH$_2$—CH$_2$—CH$_2$—CO—CH$_3$ is obtained.

The structure of the products obtained is confirmed by the infrared spectrum, mass spectrum, and proton nuclear magnetic resonance spectrum.

EXAMPLE 4

The mixture obtained at the end of Example 3 (1 g; i.e. 5.2 millimoles), methanol (10 cc) and palladium on charcoal containing 10% of palladium (0.3 g) are introduced into a 125-cc stainless steel autoclave. After purging with nitrogen, a hydrogen pressure of 50 bars is established. The mixture is shaken at 50° C. for 12 hours. After filtration and evaporation of the solvent, hexahydropseudoionone (0.7 g; 3.5 millimoles), of formula:

(CH$_3$)$_2$CH—CH$_2$—CH$_2$—CH$_2$—CH(CH$_3$)—CH$_2$—CH$_2$—CH$_2$—CO—CH$_3$ the structure of which is confirmed by the mass spectrum and the $^{13}$C nuclear magnetic resonance spectrum, is obtained in 67% yield.

EXAMPLE 5

Into a 50-cc round flask are introduced, under an argon atmosphere: dry toluene (10 cc), the mixture obtained at the end of Example 3 (610 mg) and RhCO (triphenyl phosphine)$_3$ (25.7 mg). The mixture is left to react under reflux for 48 hours.

Analysis by gas phase chromatography shows the presence of a mixture of cis and trans pseudoionones of formula:

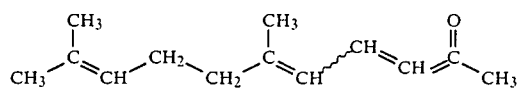

We claim:
1. 2-Methyl-6-methylene-1,3,7-octatriene of formula:

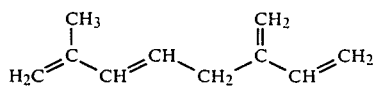

2. A process for preparing 2-methyl-6-methylene-1,3,7-octatriene as claimed in claim 1, which comprises dehydrochlorinating 3-chloro-2-methyl-6-methylene-1,7-octadiene of formula:

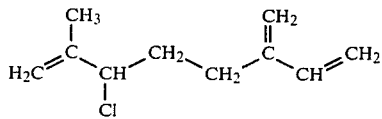

in the presence of a catalyst based on divalent palladium or on palladium(O) combined with a ligand and of an inorganic base.

3. Process according to claim 2, in which the catalyst is chosen from $PdCl_2$, $Pd(OCOCH_3)_2$, $Pd(NO_3)_2$, $Pd(acetylacetonato)_2$, $PdCl_2[P(C_6H_5)_3]_2$, $PdCl_2(C_6H_5-CN)_2$, $PdCl_2(CH_3-CN)_2$, $[C_3H_5PdCl]_2$, $[C_3H_5PdOCOCH_3]_2$, $(C_3H_5)_2Pd$, $Pd(dibenzylidene acetone)_2$ and a $PdL_4$ derivative in which L denotes a ligand chosen from phosphines, diphosphines, phosphites, arsines and stibines.

4. Process according to claim 2, in which the said base is an alkali metal hydroxide.

5. Process according to claim 2, in which the dehydrochlorination is carried out in an anhydrous ether or aromatic hydrocarbon.

6. Process according to claim 2, in which the dehydrochlorination is carried out at a temperature below 25° C.

7. Process according to claim 2 in which the dehydrochlorination is carried out in the presence of a quaternary ammonium salt.

* * * * *